United States Patent
Rolston

(10) Patent No.: US 6,916,341 B2
(45) Date of Patent: Jul. 12, 2005

(54) DEVICE AND METHOD FOR BICOMPARTMENTAL ARTHROPLASTY

(76) Inventor: Lindsey R. Rolston, 2120 Forest Ridge Pkwy., Suite 240, New Castle, IN (US) 47362

( * ) Notice: Subject to any disclaimer, the term of this patent is extended or adjusted under 35 U.S.C. 154(b) by 143 days.

(21) Appl. No.: 10/370,002

(22) Filed: Feb. 20, 2003

(65) Prior Publication Data

US 2004/0167630 A1 Aug. 26, 2004

(51) Int. Cl.$^7$ ................................................. A61F 2/38
(52) U.S. Cl. ................... 623/20.3; 623/20.19; 623/20.15
(58) Field of Search ........................... 623/20.14–20.33, 623/20.35, 14.12

(56) References Cited

U.S. PATENT DOCUMENTS

| | | | |
|---|---|---|---|
| 5,092,895 A | 3/1992 | Albrektsson et al. | |
| 5,314,482 A | 5/1994 | Goodfellow et al. | |
| 5,336,266 A | 8/1994 | Caspari et al. | |
| 5,520,695 A | 5/1996 | Luckman | |
| 5,702,459 A | 12/1997 | Hummer et al. | |
| 5,702,467 A | 12/1997 | Gabriel et al. | |
| 5,738,686 A | 4/1998 | Kubein-Meesenburg et al. | |
| 6,074,425 A | 6/2000 | Pappas | |
| 6,482,209 B1 | 11/2002 | Engh et al. | |
| 6,749,638 B1 * | 6/2004 | Saladino | 623/20.14 |
| 2001/0039455 A1 | 11/2001 | Simon et al. | |
| 2002/0068979 A1 | 6/2002 | Brown et al. | |
| 2002/0173852 A1 | 11/2002 | Felt et al. | |
| 2002/0198528 A1 | 12/2002 | Engh et al. | |
| 2003/0158606 A1 * | 8/2003 | Coon et al. | 623/20.15 |
| 2003/0225457 A1 * | 12/2003 | Justin et al. | 623/20.14 |
| 2004/0102852 A1 * | 5/2004 | Johnson et al. | 623/20.15 |
| 2004/0153162 A1 * | 8/2004 | Sanford et al. | 623/20.3 |
| 2004/0204760 A1 * | 10/2004 | Fitz et al. | 623/14.12 |

* cited by examiner

Primary Examiner—Bruce Snow
Assistant Examiner—Cheryl Miller
(74) Attorney, Agent, or Firm—Jay G. Taylor; Homer W. Faucett, III; Ice Miller

(57) ABSTRACT

Disclosed is a device and method of bicompartmental arthroplasty of the knee. The device permits arthroplasty of the medial or lateral and patellofemoral compartments of the knee while leaving the opposite compartments and the anterior and posterior cruciate ligaments intact. The device provides a femoral prosthesis component that includes a trochlear surface and a tibial prosthesis component which can be secured to the tibia. The femoral component is essentially "u" shaped having an anterior leg upon which the trochlear surface is positioned and a posterior leg which engages the posterior surface of the distal end of the femur. The femoral component also has a convex articulating surface which engages a concave articulating surface of the tibial prosthesis component to approximate the articulation of a healthy knee.

46 Claims, 10 Drawing Sheets

DEVICE AND METHOD FOR BICOMPARTMENTAL ARTHROPLASTY

FIELD OF THE INVENTION

This invention relates to a device and method for bicompartmental arthroplasty for resurfacing of either the medial joint and the patellofemoral joint of the knee or the lateral and patellofemoral joint of the knee in order to treat the pain associated with arthritis. The present device and method resurfaces either the medial or lateral joints depending on which compartment is diseased, but does not resurface both the lateral (outside) and medial (inside) compartment of the knee at the same time.

BACKGROUND OF THE INVENTION

Total knee joint replacement (arthroplasty) is a common and very successful surgery for people with degenerative arthritis (osteoarthritis) of the knee. Over 200,000 patients a year in the United States undergo total knee replacement surgery. Total knee replacement puts an artificial surface on all parts of the knee joint that contact each other as the knee bends. The damaged cartilage is removed, a small amount of bone is removed, the knee implant is attached to the distal end of the femur and proximal end of the tibia, and the patella is resurfaced if necessary. The implant typically is made of metal and plastic and provides an artificial articulating surface which causes no pain to the patient. Unfortunately total knee replacement results in sacrifice of the anterior and posterior cruciate ligaments.

More recently, unicompartmental knee arthroplasty has been utilized where there is arthritic damage to only a single compartment of the knee and no damage to the other compartments. The inside (medial) component (medial tibial plateau and the medial femoral condyle) is most commonly involved and replaced using unicompartmental arthroplasty. However, occasionally, the outside (lateral) compartment (the lateral tibial plateau and the lateral femoral condyle) is sometimes involved and must be replaced. Also the knee cap, i.e., the patellofemoral compartment (the patella and femoral trochlear notch) may also develop osteoarthritis. Heretofore, if more than a single compartment of the knee had arthritic disease, total knee replacement was the only available treatment. The present invention provides a device and method for bicompartmental arthroplasty which permits the resurfacing of the medial and patellofemoral joints of the knee or the lateral and patellofemoral joints without the necessity for resurfacing of the opposite compartment of the knee or the sacrifice of the anterior or posterior cruciate ligaments.

BRIEF DESCRIPTION OF THE INVENTION

A device for bicompartmental arthroplasty of a patient's knee in accordance with the present invention comprises a femoral prosthesis component configured to resurface the patellofemoral and one other compartment of the knee i.e., either the medial compartment or the lateral compartment depending on which compartment is diseased. The femoral prosthesis component has a first internal surface configured to be secured to a surgically prepared distal end of the one other compartment of the patient's femur so that the anterior and posterior cruciate ligaments remain intact. The femoral prosthesis component also has a second exterior convex curved surface positioned and configured to replicate a femoral condyle for that compartment and a concave trochlea surface positioned and configured to articulate with the patella. The device also comprises a tibial prosthesis component configured for the one other compartment of the knee having a first interior surface configured to be secured to a surgically prepared proximal end of the one other compartment of the patent's tibia and a second concave curved exterior surface configured to receive the second convex curved surface of the femoral prosthesis component to permit pivotal articulation between said femoral prosthesis component and the tibial prosthesis component, approximating the articulation of a healthy knee joint.

A method of performing bicompartmental arthroplasty of a patellofemoral and one other compartment of a patient's knee comprises the steps of making an incision along the anterior aspect of the one other compartment of the knee, excising the remnants of the meniscus of the one other compartment, surgically preparing a proximal end of the one other compartment of the patient's tibia to receive a tibial prosthesis component in a manner so as to preserve the integrity of the anterior and posterior cruciate ligaments. The tibial prosthesis component has a first surface configured to be secured to the surgically prepared one other compartment of the proximal end of the tibia and a second concave curved surface. Next the patella is rotated approximately 90 degrees. The distal end of the one other compartment of a the patient's femur is surgically prepared to receive a femoral prosthesis component. The femoral prosthesis component has a concave trochlea surface and a first surface configured to be secured to the surgically prepared one other compartment of the distal end of the femur. The femoral component also has a second convex curved surface configured to replicate the condyle and articulate with the second concave curved surface of the tibial prosthesis component to permit pivotal articulation between the femoral prosthesis component and the tibial prosthesis component in a manner approximating the articulation of a healthy knee joint. The femoral component is next secured to the femur and the tibial component is secured to the tibia. The patella is positioned over the concave trochlea surface of the femoral prosthesis component and the incision is closed.

If the patella is also diseased, the method also comprises the additional steps of surgically preparing a posterior surface of the patent's patella to receive a patella prosthesis component having a first surface configured to be secured to the surgically prepared posterior surface of the patella, and a convex curved second surface configured to engage the concave trochlea surface of the femoral prosthesis component, and securing the patella prosthesis component to the patella.

DETAILED DESCRIPTION OF THE PREFERRED EMBODIMENTS

Figure 1A:
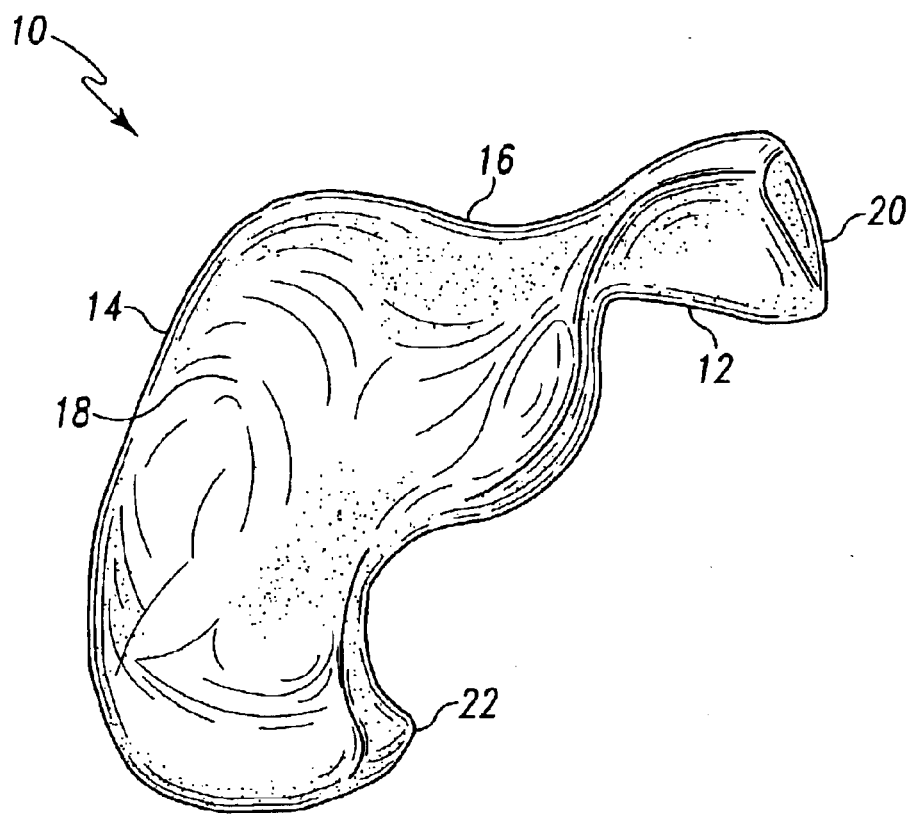
FIG. 1A is a perspective view of the articular surface of a medial femoral prosthesis component in accordance with the present invention.
Figure 2:
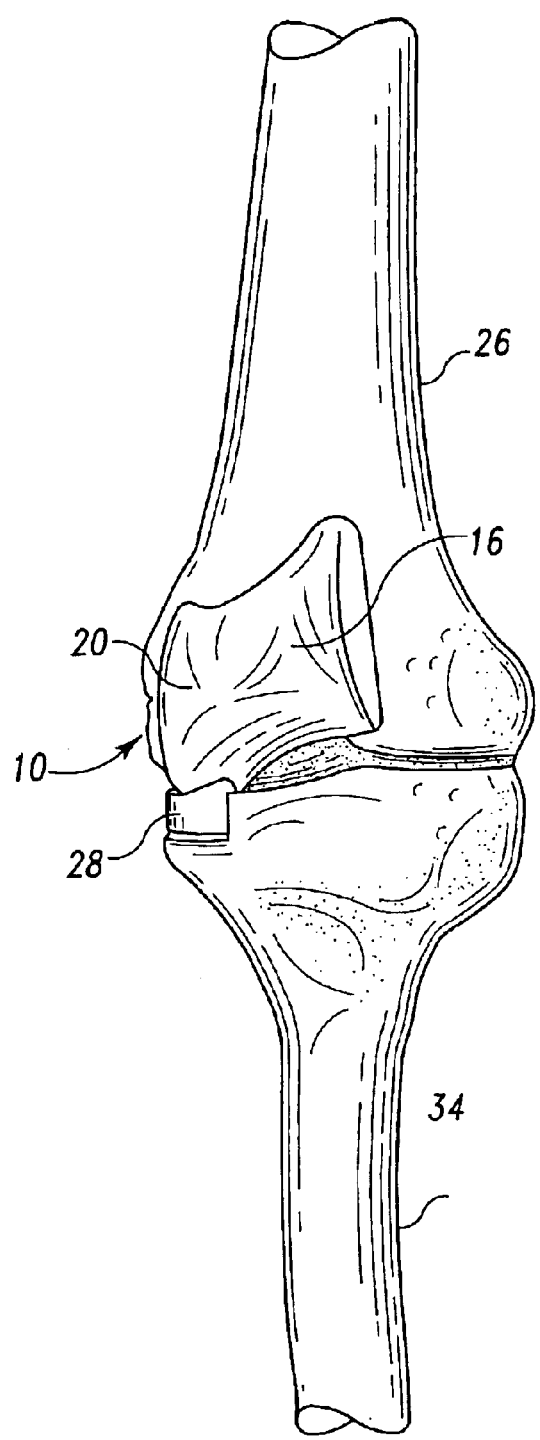
FIG. 2 is a front view of the medial femoral prosthesis component of FIG. 1 and a medial tibial prosthesis component of the present invention as surgically implanted on a human knee.

FIGS. 1A and B illustrate a medial femoral prosthesis component 10 for use in connection with a combination device for bicompartmental arthroplasty of the knee. The prosthesis 10 is essentially u-shaped with one leg of the "u" forming the anterior (front) portion 20 of the prosthesis and the other leg of the "u" forming the posterior (rear) portion 22 of the prosthesis and a base portion 21 connecting the anterior and posterior portions 20 and 22. The medial femoral prosthesis component 10 has an interior first surface 12 which is configured to be secured to a surgically prepared portion of the distal end of the medial compartment of the femur 26 as shown in FIG. 2 as will be described in more detail below. The exterior surface 14 of component 10 has a concave trochlear groove 16 formed on the anterior surface of the leg 20 of prosthesis component 10. A convex second surface 18 is formed on the medial side of the base portion 21 of prosthesis 10 and is configured to replicate the medial femoral condyle of the knee. A post 13 is mounted to the interior surface 12 of base portion 21 and extends essentially perpendicularly from that surface. Post 13 is inserted into a hole drilled in the femur during surgical preparation to aid in securing the component 10 to the femur 26. More than one post 13 could be mounted to device 10 as necessary.

Figure 3:
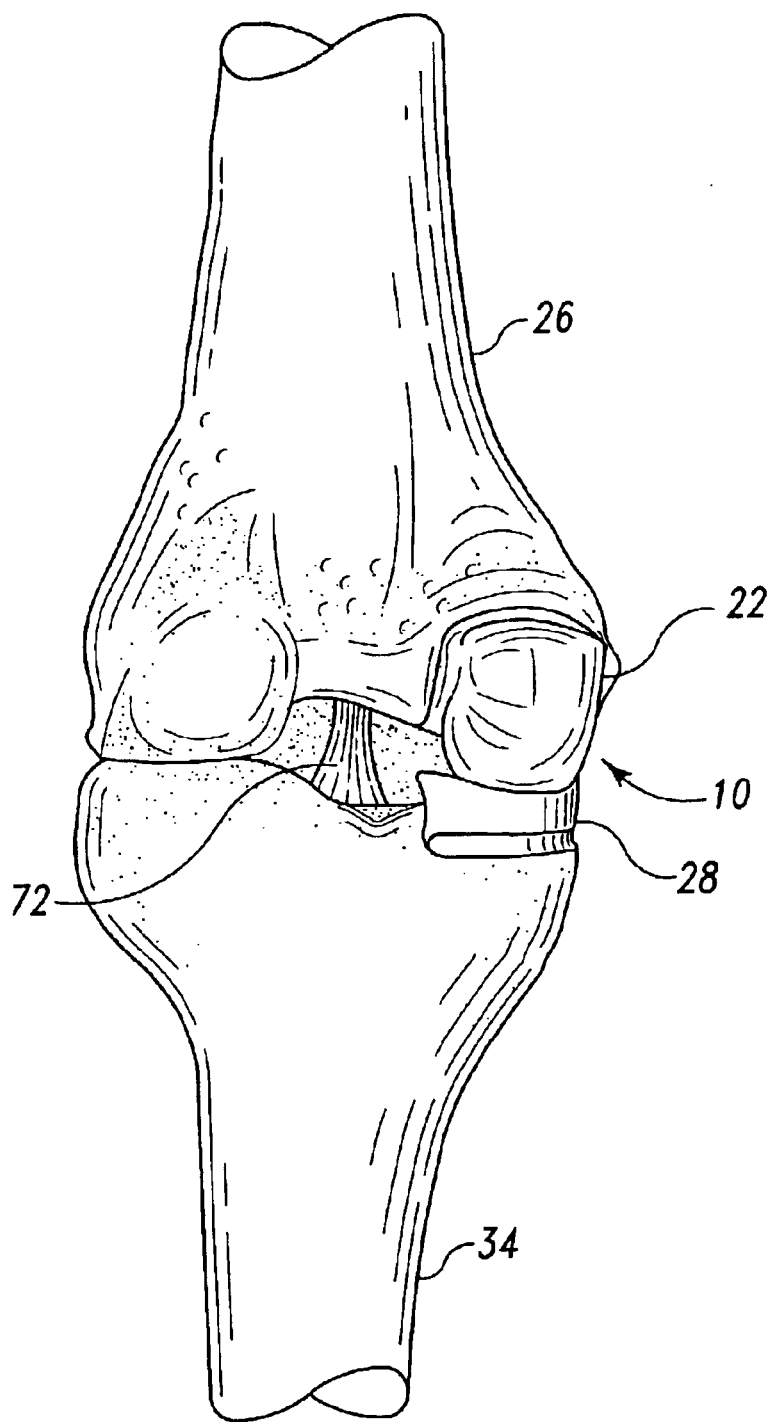
FIG. 3 is a rear view of a device for bicompartmental arthroplasty of the knee in accordance with the present invention as surgically implanted on a human knee.

With reference to FIG. 2, the prosthesis component 10 is shown in position as it would be on the distal end of the femur 26 of the human knee. The anterior leg 20 of the "u" shaped medial component 10 is positioned over a surgically prepared anterior surface of the femur 26. With reference to FIG. 3, the posterior leg portion 22 of medial component 10 extends upwardly along the posterior surface of a surgically prepared medial compartment of the distal end of the femur 26. The interior first surface 12 can be textured to facilitate attachment to the femur using a cement or it may have a bone ingrowth surface applied so that the bone will grow into the ingrowth surface thereby securing component 10 to the femur. Prior to implanting, the distal end of the femur 26 is surgically prepared to remove the diseased portions of the distal end of the femur and the remnants of the medial meniscus are excised or removed. The distal end of the femur is then cut to mate with the interior surface 12 of component 10 and a hole is drilled to accommodate post 13.

Figure 8:
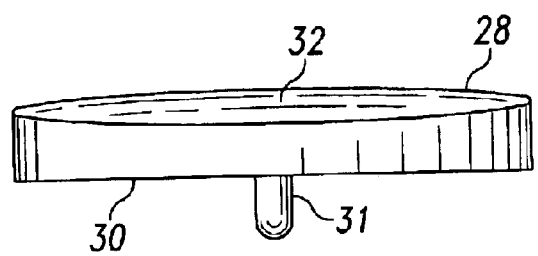
FIG. 8 is a side view of one type of medial tibial prosthesis component for use in connection with the present invention.
Figure 9:
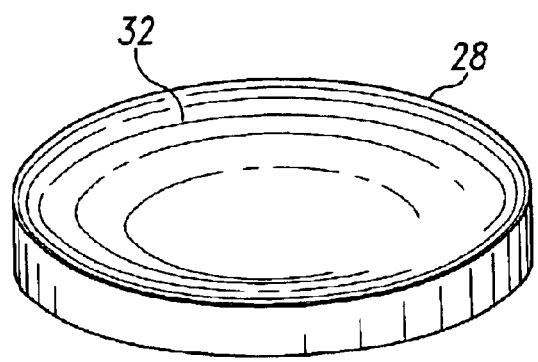
FIG. 9 is an upper side perspective view of the prosthesis of FIG. 8.

With reference to FIG. 2, a medial tibial prosthesis component 28 is shown secured to a surgically prepared portion of the proximal end of the tibia. With reference to FIGS. 8 and 9, the medial tibial component 28 has a first flat surface 30 and a second concave surface 32. The concave surface 32 of the medial tibial component 28 is configured to articulate with the convex second surface of the medial femoral component 10. Flat surface 30 has a post 31 extending perpendicularly from that surface and is configured and adapted to be secured to a surgically prepared portion of the medial compartment of the tibia 34. Flat surface 30 can be textured to facilitate attachment by cement or it can have a bone ingrowth surface applied so that the bone will grow into the ingrowth surface thereby securing the component 28 to the tibia. As illustrated in FIGS. 2 and 3, a portion of the tibial plateau is surgically removed so that the medial component 28 can be attached. The medial tibial component 28 illustrated in FIGS. 8 and 9 is comprised entirely of a plastic material that is biomedically compatible with the human body.

Figure 10:
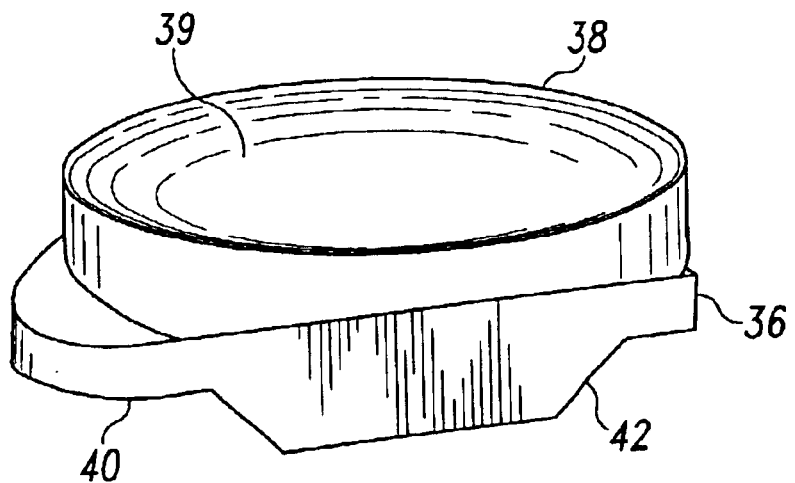
FIG. 10 is an upper side perspective view of an alternative medial tibial prosthesis component that may be used in connection with the present invention.
Figure 11:
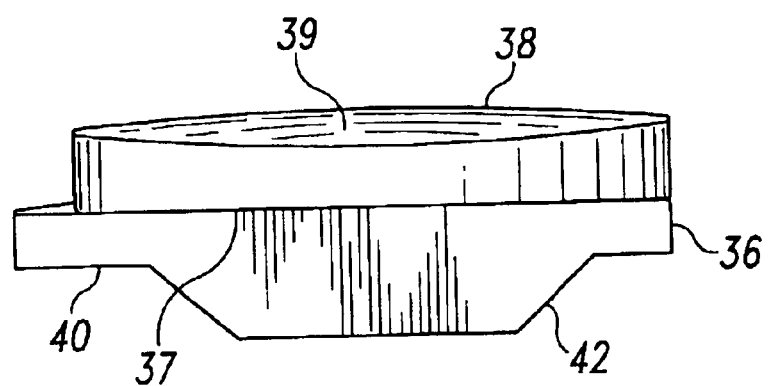
FIG. 11 is a side view of the prosthesis shown in FIG. 10.

FIGS. 10 and 11 illustrate an alternative embodiment of a medial tibial prosthesis component for use in connection with the present invention. The FIGS. 10 and 11 component comprises a flat metallic base 36 to which a plastic insert 38 with a flat base 37 and a concave upper surface 39 is attached either rigidly to or to allow rotation or movement upon the fixed base plate 37. The plastic insert 38 can be formed of the same plastic materials as component 28 illustrated in FIGS. 8 and 9. Metal base portion 36 has a flat first surface 40 and a downwardly extending flange 42 along one edge which is designed and configured to extend into a corresponding groove cut into the posterior surface of the tibia so as to aid in securing base section 36 to the tibia. Surface 40 can either be textured to aid in securing base portion 36 to the tibia using a cement, or a bone ingrowth surface can be applied to surface 40 so that base portion 36 can be secured to the tibia by bone growth into the bone ingrowth surface.

Figure 5:
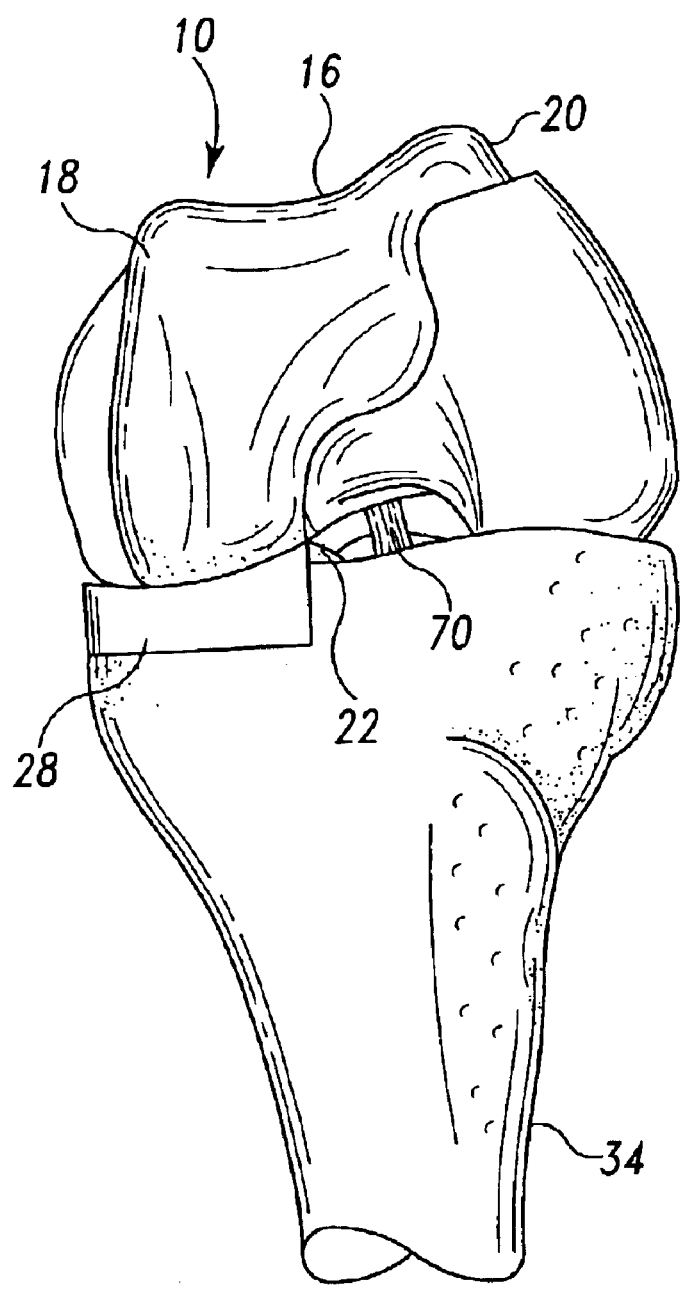
FIG. 5 is a front view of a human knee flexed 90° showing the medial femoral prosthesis component and the medial tibial prosthesis component implanted on the knee.

It can be appreciated from FIGS. 2, 3 and 5 that the lateral compartment of the knee remains in its natural state due to the fact that device 10 is affixed only to the medial compartment of the knee. Consequently, the anterior and posterior cruciate ligaments 70 and 72 remain intact and are not compromised by the device 10 or its implantation.

Figure 4:
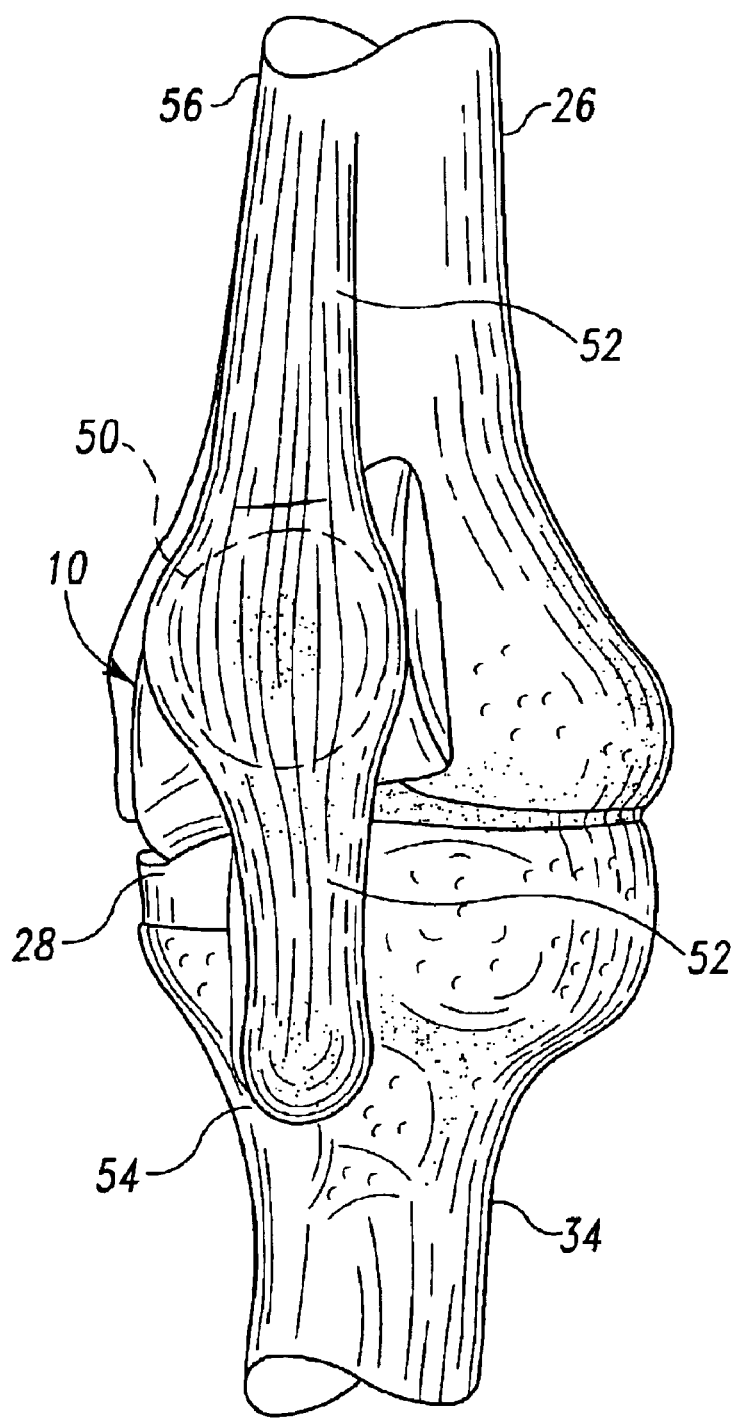
FIG. 4 is a front view of a device for bicompartmental arthroplasty in accordance with the present invention as implanted on a human knee showing the position of the patella on the device.
Figure 6:
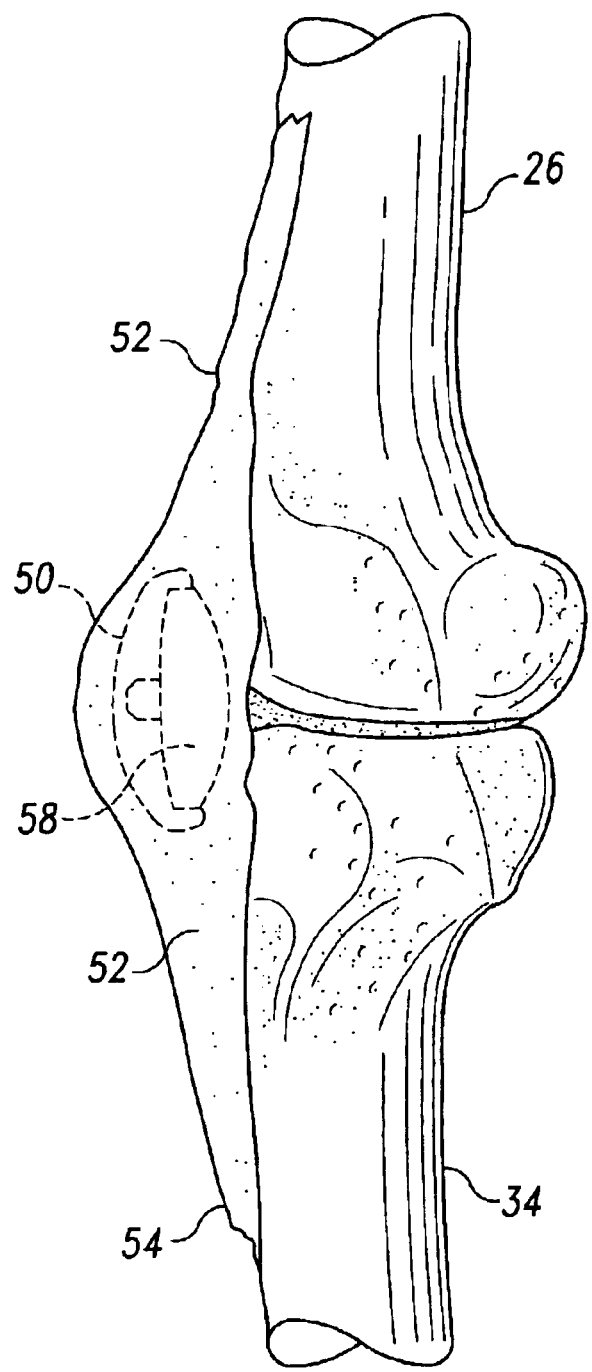
FIG. 6 is a lateral side view of a knee showing the positioning of the patella and a patella prosthesis component.

With reference to FIGS. 4 and 6, patella 50 is shown in its normal position in the trochlear groove 16 of medial femoral component 10. The patellar tendon 52 covers the patella and is attached at one end 54 to the anterior surface of the tibia and the other end 56 to the quadriceps muscle (not shown). Contraction of the quadriceps muscles pulls the patella through the trochlear groove, thereby lifting the tibia.

Figure 7:
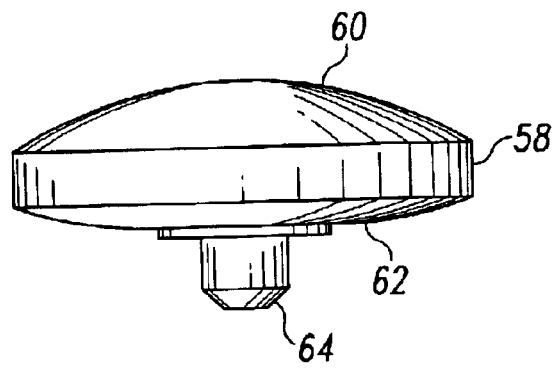
FIG. 7 is a side view of a patella component that may be used in conjunction with the present invention.

If there is arthritic disease of the patella, it may be necessary to replace the diseased posterior surface of the patella with a plastic prosthesis component. With reference to FIG. 6, patella 50 is shown in dotted lines under the patellar tendon 52. Also shown in dotted lines is a patellar component 58 as it would be positioned in a surgically prepared posterior surface of the patella 50. With reference to FIG. 7, a side view of a patella prosthesis component 58 is shown. Patella component 58 is configured to have a convex surface 60 configured and dimensioned to engage and articulate in the trochlea surface 16 of the medial femoral prosthesis component 10. Patellar insert component 58 also comprises a surface 62 which includes a post 64 configured and adapted to be secured to a surgically prepared posterior surface of the patella.

As discussed above, the interior surface 12 of femoral component 10 can either be configured to be secured to the femur by the use of a cement, or a bone ingrowth surface may be applied to the interior surface 12 so that the femur bone will grow into and more permanently secure the femoral component to the femur. Such bone ingrowth surfaces are well-known in the art and have previously been used in connection with both unicompartmental and full knee replacement prosthesis. Similarly, the medial tibial prosthesis component 28 can either be secured to the tibia by use of a cement or also by the use of a bone ingrowth surface applied to the tibial component so that the bone structure of the tibia will grow into the bone ingrowth surface to more permanently secure the tibial component to the tibia.

With reference to FIGS. 3 and 5, it can be seen that the present invention can be implanted in the knee without disturbing or damaging the middle third of the knee joint where the anterior cruciate ligament 70 and the posterior cruciate ligament 72 are located. Thus, the present invention allows a bicompartmental knee arthroplasty that preserves the integrity of the anterior and posterior cruciate ligaments.

To implant the FIG. 1–4 embodiment in a patient, a 3 to 4 inch longitudinal incision is made on the anterior aspect of the knee from the medial aspect of the patellar tendon 1 centimeter below the joint line extending approximately 3 to 4 inches in a vertical fashion. The incision is opened along the length of the incision with a medial parapatellar arthrotomy extending in a minimal fashion into the quadriceps femoris muscle medially. The remnants of the medial meniscus are excised. A portion of the fat pad is excised with care being taken to preserve the integrity of the anterior and posterior cruciate ligaments.

Surface cuts are made on the medial tibial articular surface using the technology previously employed by the Accuris® unicompartmental arthroplasty of Smith and Nephew Orthopedics, Inc. After the tibial cut is made, the patella is subluxed or rotated 90°. The intramedullary canal at the distal end of the femur is exposed using a ⅜ inch drill bit. An intramedullary rod is inserted into the distal femur until a distal femoral cutting block is flush against the distal medial femur. A distal femoral cutting block of the appropriate angle is attached after the cutting block is pinned in place, the distal femoral cut is made with an oscillating saw. The jig is removed and a sizing block is placed against the distal femur in order to reference the posterior medial femoral condyle. A stylus is attached in order to reference the anterior thickness of the distal femur and the appropriate size of the femoral prosthesis 10 is selected, the appropriate femoral cutting block is attached to the intramedullary rod in the appropriate rotation. The block is pinned and the distal anterior cutting block is used to remove the anterior surface of the distal femur.

Anterior and posterior chamfer cuts are made from the medial aspect of the distal femur followed by a posterior femoral cut for the medial femoral condyle. The anterior chamfer cut is extended over the medial aspect of the lateral femoral condyle and a sagittal saw using a freehand technique is used to complete the trochlear cut.

Next, a trial reduction with the femoral component 10 and tibial component 28 is employed to assure correct surgical preparation and sizing. The extent of possible arthritic disease of the patella is next assessed. If there is extensive disease of the patella, the patella is rotated approximately 90° and an inset patella reamer is applied to the posterior surface of the patella and the patella is reamed to permit the inset of a patella prosthesis component 58. Alternatively, an onset or a mobile bearing patella prosthesis may be used as is well known in the art.

A partial lateral facetectomy is typically performed to limit the patellar contact with the transition zone of the distal femur and the femoral component 10. The patellar implant 58 should be medialized to assist with patella tracking. Release of the medial collateral ligament can be employed as necessary to allow for ligamentous balancing of the arthroplasty.

The femoral tibial and patellar implants 10 and 28 are next either cemented in the usual fashion if the trial reduction is found to be satisfactory or securely placed over the prepared bone surface so that bone ingrowth can occur if the components have a bone ingrowth surface applied. The knee capsule is closed with a non-absorbable suture followed by skin closure and sterile metal staples with sterile dressing.

Figure 12:
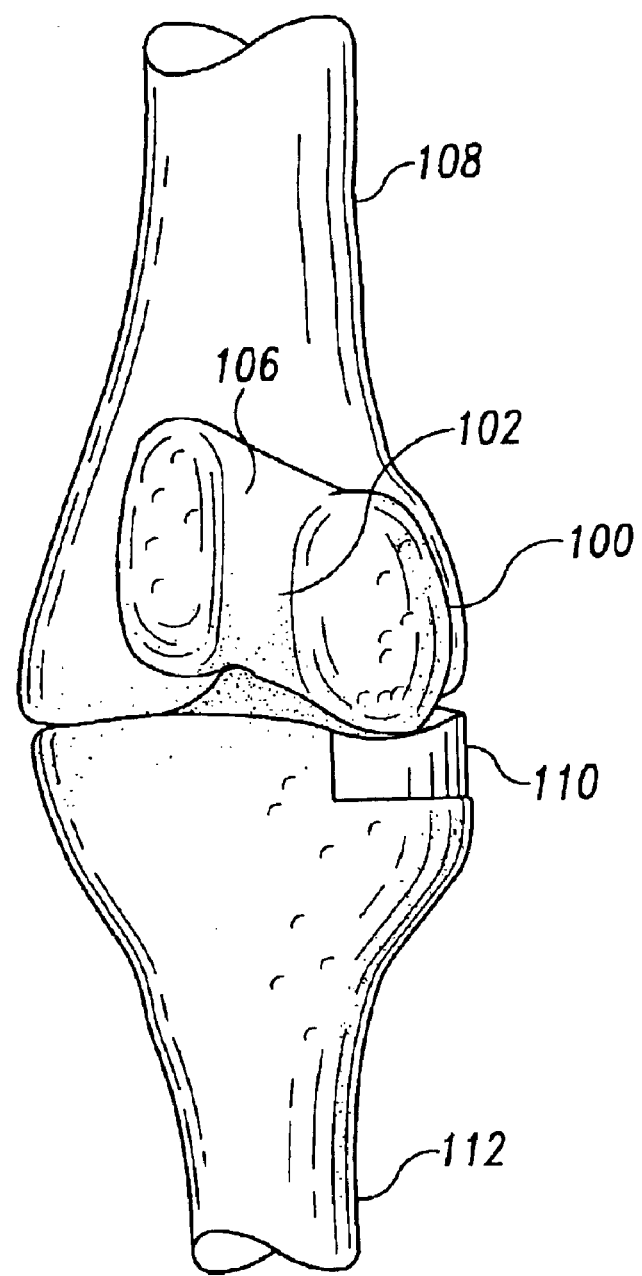
FIG. 12 is a front view of an alternative embodiment of the present invention for the lateral compartment of the knee as implanted on a human knee.
Figure 13:
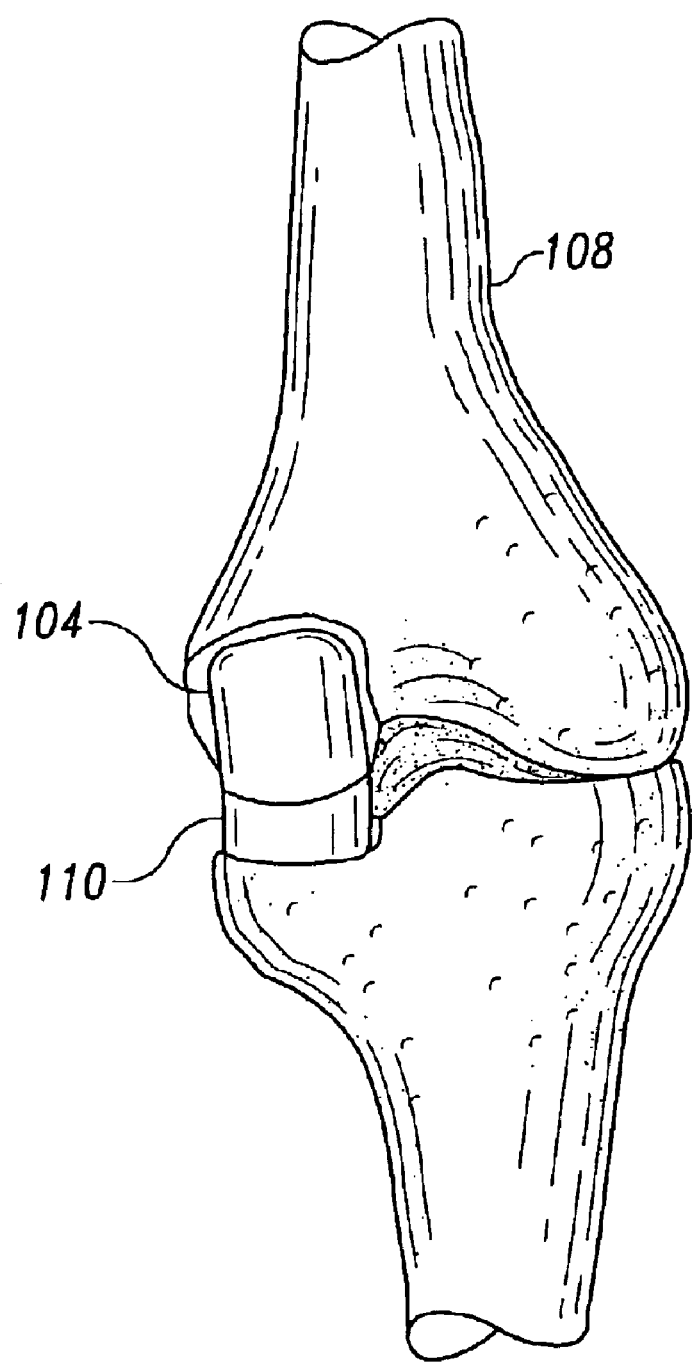
FIG. 13 is a rear view of the embodiment of FIG. 12.

With reference to FIGS. 12 and 13, an alternative embodiment of the present invention is shown. While in most cases, the medial compartment of the knee is more prone to be subject to arthritic disease than the lateral compartment, in some cases, the lateral compartment may be diseased while the medial compartment remains healthy and unaffected. This alternative embodiment is designed for those situations where the lateral and patellofemoral joints are affected, but the medial compartment is not.

Figure 1B:
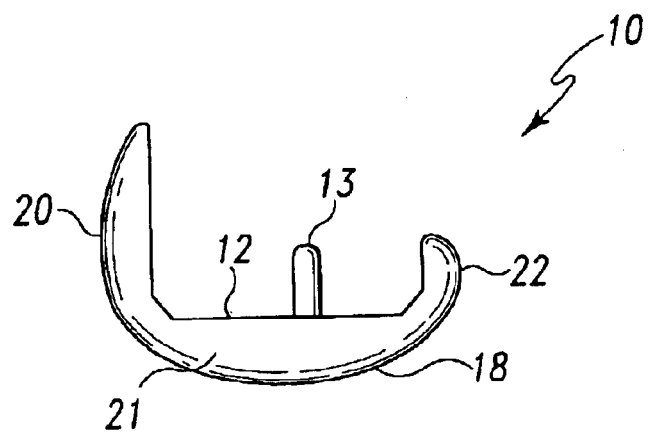
FIG. 1B is a side view of the medial femoral prosthesis component of FIG. 1.

A lateral femoral prosthesis component 100 similar to the medial femoral prosthesis component 10 of FIG. 1 except it is configured for the lateral compartment rather than the medial compartment. Lateral femoral prosthesis component 100 is essentially "u" shaped having a first anterior leg portion 102 and a second posterior leg portion 104 that are joined by a base portion (not shown). Anterior leg portion 102 has a trochlear groove 106 formed on the face thereof to receive and articulate with the patella. Lateral femoral prosthesis component 100 has an interior surface within the "u" (not shown) similar to the interior surface 12 of component 10 that can be secured to a surgically prepared portion of the lateral compartment of the femur 108 using either a cement or a bone ingrowth surface as describe previously.

A lateral tibial prosthesis component 110 similar to the medial tibial component 28 of FIGS. 1–4 is shown in FIGS. 12 and 13 as implanted on a surgically prepared lateral compartment of tibia, 112. Component 110 has a flat bottom surface and a concave upper surface that receives and articulates with a convex outer surface (not shown) on the base portion of the femoral prosthesis component 100 in the same manner as describe previously with respect to the FIG. 1 embodiment. Also, tibial component 110 can be fabricated from both metal base and a plastic insert as shown in FIGS. 10 and 11.

Femoral component 100 and tibial component 110 are also configured and designed so that they can be implanted without causing any damage to the middle portion of the knee so that the anterior and posterior cruciate ligaments remain intact after implantation.

It should be appreciated that both femoral prosthesis components 10 and 100 and tibial prosthesis components 28 and 110 can be fabricated from either a metallic material or from plastic. Typically, one component is fabricated from one material and the opposing component is fabricated from the other material so that there is a metal on plastic articulating joint for wear purposes. However, both parts could be fabricated from the same material. A variety of metallic materials can be used including but not limited to stainless steel, cobalt chrome steel, titanium, Zirconia, ceramics and tantalum. Also, a variety of plastic materials can be used including but not limited to polyethylene, polycarbonate-based polyurethane, and implantable-grade polymethyl methacrylate (PMMA).

It should be recognized that the preferred embodiment of the present invention as described above can be varied or modified without departing from the spirit and scope of the present invention as described and claimed in the following claims.

I claim:

1. A device for bicompartmental arthroplasty of the knee comprising:

a monolithically formed medial, but not lateral, femoral prosthesis component having a first internal surface configured to be secured to a surgically prepared medial compartment of a distal end of a patient's femur and a second exterior convex curved surface positioned and configured to replicate a medial femoral condyle; said medial femoral prosthesis component also having a concave trochlea surface positioned and configured to articulate with the patella; and a unicondyle medial tibial prosthesis component having a first interior surface configured to be secured to a surgically prepared medial compartment of a proximal end of the patent's tibia and a second concave curved exterior surface configured to receive the second convex curved surface of said medial femoral prosthesis component to permit pivotal articulation between said medial femoral prosthesis component and said medial tibial prosthesis component, said pivotal articulation approximating the articulation of a healthy knee joint.

2. A device for bicompartmental arthroplasty of the knee as claimed in claim 1 where in said medial femoral prosthesis component is made of metallic material.

3. A device for bicompartmental arthroplasty of the knee as claimed in claim 1 where in said medial femoral prosthesis component is made of a bio-compatible plastic.

4. A device for bicompartmental arthroplasty of the knee as claimed in claim 1 where in said medial tibial prosthesis component is made of a bio-compatible plastic.

5. A device for bicompartmental arthroplasty of the knee as claimed in claim 1 where in said medial tibial prosthesis component is made of metallic material.

6. A device for bicompartmental arthroplasty of the knee as claimed in claim 1 where in said medial tibial prosthesis component is made of both a bio-compatible plastic and metallic material.

7. A device for bicompartmental arthroplasty of the knee as claimed in claim 1 where in said medial femoral prosthesis component and said medial tibial prosthesis component are configured and dimensioned to permit the distal end of the femur and the proximal end of the tibia to be surgically prepared in manner so as to preserve the integrity of the anterior and posterior cruciate ligaments.

8. A device for bicompartmental arthroplasty of the knee as claimed in claim 1 where in the device is configured and dimensioned to permit the distal end of the femur and the proximal end of the tibia to be surgically prepared while the patella is rotated a approximately 90 degrees.

9. A device for bicompartmental arthroplasty of the knee as claimed in claim 1 further comprising a patella prosthesis component having a first surface configured to be secured to a surgically prepared posterior surface of the patella, and a convex curved second surface configured to articulate with the concave trochlea surface of said medial femoral prosthesis component.

10. A device for bicompartmental arthroplasty of the knee as claimed in claim 9 wherein said patella prosthesis component is configured to be secured to the patella by cement.

11. A device for bicompartmental arthroplasty of the knee as claimed in claim 9 wherein said patella prosthesis component is configured to be secured to the patella by bone ingrowth into an ingrowth surface on the first internal surface of the patella prosthesis component.

12. A device for bicompartmental arthroplasty of the knee as claimed in claim 1 wherein said femoral prosthesis component is configured to be secured to the femur by a cement.

13. A device for bicompartmental arthroplasty of the knee as claimed in claim 1 wherein said femoral prosthesis component is configured to be secured to the femur by bone ingrowth into an ingrowth surface on the first internal surface of the femoral prosthesis component.

14. A device for bicompartmental arthroplasty of the knee as claimed in claim 1 wherein said tibial prosthesis component is configured to be secured to the tibia by a cement.

15. A device for bicompartmental arthroplasty of the knee as claimed in claim 1 wherein said tibial prosthesis component is configured to be secured to the tibia by bone ingrowth into an ingrowth surface on the first interior surface of the tibial prosthesis component.

16. A device for bicompartmental arthroplasty of the knee comprising:

a monolithically formed medial, but not lateral, femoral prosthesis component having a first leg portion and a second leg portion and a base portion connected between said first and second leg portions to form an essentially U shaped component, said medial femoral prosthesis component having a first interior surface comprising a base interior surface, and anterior interior surface and a posterior interior surface, said anterior interior surface and said posterior interior surfaces being essentially parallel to one another and being configured to be secured to a surgically prepared medial compartment of a distal end of the patient's femur so that the base interior surface contacts the distal end of the femur, said anterior interior surface contacts an anterior surface of the distal end of the femur, and the posterior interior surface contacts a posterior surface of the distal end of the femur, and said medial femoral prosthesis component also having a second exterior convex curved surface on said base portion positioned and configured to replicate a medial femoral condyle, and a concave trochlea surface positioned on said first leg portion and configured to articulate with the patella; and a unicondyle medial tibial prosthesis component having a first surface configured to be secured to a surgically prepared medial compartment of the proximal end of the tibia and a second concave curved surface configured to receive the second convex curved surface of said medial femoral prosthesis component to permit pivotal motion between said medial femoral prosthesis component and said medial tibial prosthesis component, said pivotal motion approximating the motion of a healthy knee joint.

17. A device for bicompartmental arthroplasty of the knee as claimed in claim 16 where in said medial femoral prosthesis component is made of metallic material.

18. A device for bicompartmental arthroplasty of the knee as claimed in claim 16 where in said medial femoral prosthesis component is made of a bio-compatible plastic.

19. A device for bicompartmental arthroplasty of the knee as claimed in claim 16 where in said medial tibial prosthesis component is made of a bio-compatible plastic.

20. A device for bicompartmental arthroplasty of the knee as claimed in claim 16 where in said medial tibial prosthesis component is made of metallic material.

21. A device for bicompartmental arthroplasty of die knee as claimed in claim 16 where in said medial tibial prosthesis component is made of both a bio-compatible plastic and metallic material.

22. A device for bicompartmental arthroplasty of the knee as claimed in claim 16 where in said medial femoral prosthesis component and said medial tibial prosthesis component are dimensioned to permit the distal end of the femur and the proximal end of the tibia to be surgically prepared in manner so as to preserve the integrity of the anterior and posterior cruciate ligaments.

23. A device for bicompartmental arthroplasty of the knee as claimed in claim 16 where in the device is dimensioned to permit the distal end of the femur and the proximal end of the tibia to be surgically prepared while the patella is rotated approximately 90 degrees.

24. A device for bicompartmental arthroplasty of the knee as claimed in claim 16 further comprising a patella prosthesis component having a first surface configured to be secured to a surgically prepared posterior surface of the patent's patella, and a convex curved second surface configured to engage the concave trochlea surface of said medial femoral prosthesis component.

25. A device for bicompartmental arthroplasty of the knee as claimed in claim 24 wherein said patella prosthesis component is configured to be secured to the patella by cement.

26. A device for bicompartmental arthroplasty of the knee as claimed in claim 24 wherein said patella prosthesis component is configured to be secured to the patella by bone ingrowth into an ingrowth surface on the first surface of the patella prosthesis component.

27. A device for bicompartmental arthroplasty of the knee as claimed in claim 16 wherein said femoral prosthesis component is configured to be secured to the femur by a cement.

28. A device for bicompartmental arthroplasty of the knee as claimed in claim 16 wherein said femoral prosthesis component is configured to be secured to the femur by bone ingrowth into an ingrowth surface on the first interior surface of the femoral prosthesis component.

29. A device for bicompartmental arthroplasty of the knee as claimed in claim 16 wherein said tibial prosthesis component is configured to be secured to the tibia by a cement.

30. A device for bicompartmental arthroplasty of the knee as claimed in claim 16 wherein said tibial prosthesis component is configured to be secured to the tibia by bone ingrowth into an ingrowth surface on the first interior surface of the tibial prosthesis component.

31. A device for bicompartmental arthroplasty of the knee comprising:

a monolithically formed medial, but not lateral, femoral prosthesis component having a first internal surface configured to have at least one flat surface to be secured to a surgically prepared medial compartment of a distal end of a patient's femur and a second exterior convex curved surface positioned and configured to replicate a medial femoral condyle; said medial femoral prosthesis component also having a concave trochlea surface positioned and configured to articulate with the patella; and a unicondyle medial tibial prosthesis component having a first interior surface configured to be secured to a surgically prepared medial compartment of a proximal end of the patent's tibia and a second concave curved exterior surface configured to receive the second convex curved surface of said medial femoral prosthesis component to permit pivotal articulation between said medial femoral prosthesis component and said medial tibial prosthesis component, said pivotal articulation approximating the articulation of a healthy knee joint.

32. A device for bicompartmental arthroplasty of the knee as claimed in claim 31 where in said medial femoral prosthesis component is made of metallic material.

33. A device for bicompartmental arthroplasty of the knee as claimed in claim 31 where in said medial prosthesis component is made of a bio-compatible plastic.

34. A device for bicompartmental arthroplasty of the knee as claimed in claim 31 where in said medial tibial prosthesis component is made of a bio-compatible plastic.

35. A device for bicompartmental arthroplasty of the knee as claimed in claim 31 where in said medial tibial prosthesis component is made of metallic material.

36. A device for bicompartmental arthroplasty of the knee as claimed in claim 31 where in said medial tibial prosthesis component is made of both a bio-compatible plastic and metallic material.

37. A device for bicompartmental arthroplasty of the knee as claimed in claim 31 where in said medial femoral prosthesis component and said medial tibial prosthesis component are configured and dimensioned to permit the distal end of the femur and the proximal end of the tibia to be surgically prepared in manner so as to preserve the integrity of the anterior and posterior cruciate ligaments.

38. A device for bicompartmental arthroplasty of the knee as claimed in claim 31 where in the device is configured and dimensioned to permit the distal end of the femur and the proximal end of the tibia to be surgically prepared while the patella is rotated approximately 90 degrees.

39. A device for bicompartmental arthroplasty of the knee as claimed in claim 31 further comprising a patella prosthesis component having a first surface configured to be secured to a surgically prepared posterior surface of the patella, and a convex curved second surface configured to articulate with the concave trochlea surface of said medial femoral prosthesis component.

40. A device for bicompartmental arthroplasty of the knee as claimed in claim 39 wherein said patella prosthesis component is configured to be secured to the patella by cement.

41. A device for bicompartmental arthroplasty of the knee as claimed in claim 39 wherein said patella prosthesis component is configured to be secured to the patella by bone ingrowth into an ingrowth surface on the first internal surface of the patella prosthesis component.

42. A device for bicompartmental arthroplasty of the knee as claimed in claim 31 wherein said femoral prosthesis component is configured to be secured to the femur by a cement.

43. A device for bicompartmental arthroplasty of the knee as claimed in claim 31 wherein said femoral prosthesis component is configured to be secured to the femur by bone ingrowth into an ingrowth surface on the first internal surface of the femoral prosthesis component.

44. A device for bicompartmental arthroplasty of the knee as claimed in claim 31 wherein said tibial prosthesis component is configured to be secured to the tibia by a cement.

45. A device for bicompartmental arthroplasty of the knee as claimed in claim 31 wherein said tibial prosthesis component is secured to the tibia by bone ingrowth into an ingrowth surface applied to the first surface of the tibial prosthesis component.

46. A device for bicompartmental arthroplasty of the knee an claimed in claim 31 wherein said tibial prosthesis component is configured to be secured to the tibia by bone ingrowth into an ingrowth surface on the first interior surface of the tibial prosthesis component.

* * * * *